(12) United States Patent
Haer et al.

(10) Patent No.: US 12,311,150 B2
(45) Date of Patent: May 27, 2025

(54) METHOD AND APPARATUS FOR CONTROLLED RELATIVE MOTION OF SURGICAL INSTRUMENTS AND COMPONENTS

(71) Applicant: FHC, Inc., Bowdoin, ME (US)

(72) Inventors: Frederick A. Haer, Brunswick, ME (US); John Robert Williams, Freeport, ME (US)

(73) Assignee: FHC, Inc., Bowdoin, ME (US)

( * ) Notice: Subject to any disclaimer, the term of this patent is extended or adjusted under 35 U.S.C. 154(b) by 374 days.

(21) Appl. No.: 17/356,948

(22) Filed: Jun. 24, 2021

(65) Prior Publication Data

US 2021/0316078 A1 Oct. 14, 2021

Related U.S. Application Data

(62) Division of application No. 16/275,654, filed on Feb. 14, 2019, now Pat. No. 11,071,829.

(Continued)

(51) Int. Cl.

| *A61M 5/315* | (2006.01) |
|---|---|
| *A61B 17/34* | (2006.01) |
| *A61M 5/31* | (2006.01) |
| *A61M 5/32* | (2006.01) |
| *A61M 25/01* | (2006.01) |

(Continued)

(52) U.S. Cl.
CPC ..... *A61M 5/31511* (2013.01); *A61B 17/3421* (2013.01); *A61M 5/3148* (2013.01); *A61M 5/322* (2013.01); *A61M 25/01* (2013.01); *A61B 2017/3409* (2013.01); *A61B 90/57* (2016.02); *A61F 2250/0067* (2013.01); *A61M 5/30* (2013.01)

(58) Field of Classification Search
CPC ............. A61M 5/3148; A61M 25/01; A61M 2205/10; A61M 2205/106; A61M 2209/00; A61M 2209/08; A61M 2209/082; A61M 2209/084; A61B 2017/3405; A61B 2017/3407; A61B 2017/3409; A61B 90/50; A61B 90/57
See application file for complete search history.

(56) References Cited

U.S. PATENT DOCUMENTS

| 2009/0204103 A1* | 8/2009 | Mendez | A61B 17/0057 604/506 |
|---|---|---|---|
| 2012/0083739 A1 | 4/2012 | Nelson | |

(Continued)

*Primary Examiner* — Kami A Bosworth
(74) *Attorney, Agent, or Firm* — The Webb Law Firm

(57) ABSTRACT

A system for controlling relative delivery of a therapeutic during a surgical intervention, having: a base; a frame having a proximal end and a distal end; a first subassembly having: a syringe carriage configured to interface with the frame and be moveable relative thereto; a plunger shaft having a proximal end and a distal end, the plunger shaft connected to the frame; and an instrument clamp configured to interact with the plunger shaft; and a syringe having a delivery cannula attached to a syringe body and a syringe plunger, the syringe held by the syringe carriage, where when the syringe plunger is secured to the instrument clamp, the syringe plunger is held in place by the instrument clamp such that the syringe plunger moves relative to the syringe body to cause delivery of a therapeutic as the syringe carriage moves and the delivery cannula is withdrawn.

16 Claims, 18 Drawing Sheets

Related U.S. Application Data

(60) Provisional application No. 62/631,096, filed on Feb. 15, 2018.

(51) Int. Cl.
*A61B 90/57* (2016.01)
*A61M 5/30* (2006.01)

(56) References Cited

U.S. PATENT DOCUMENTS

| | | |
|---|---|---|
| 2015/0157497 A1 | 6/2015 | Hufford et al. |
| 2015/0223832 A1 | 8/2015 | Swaney et al. |
| 2017/0151416 A1 | 6/2017 | Kutikov et al. |
| 2018/0280611 A1 | 10/2018 | Avalos et al. |

* cited by examiner

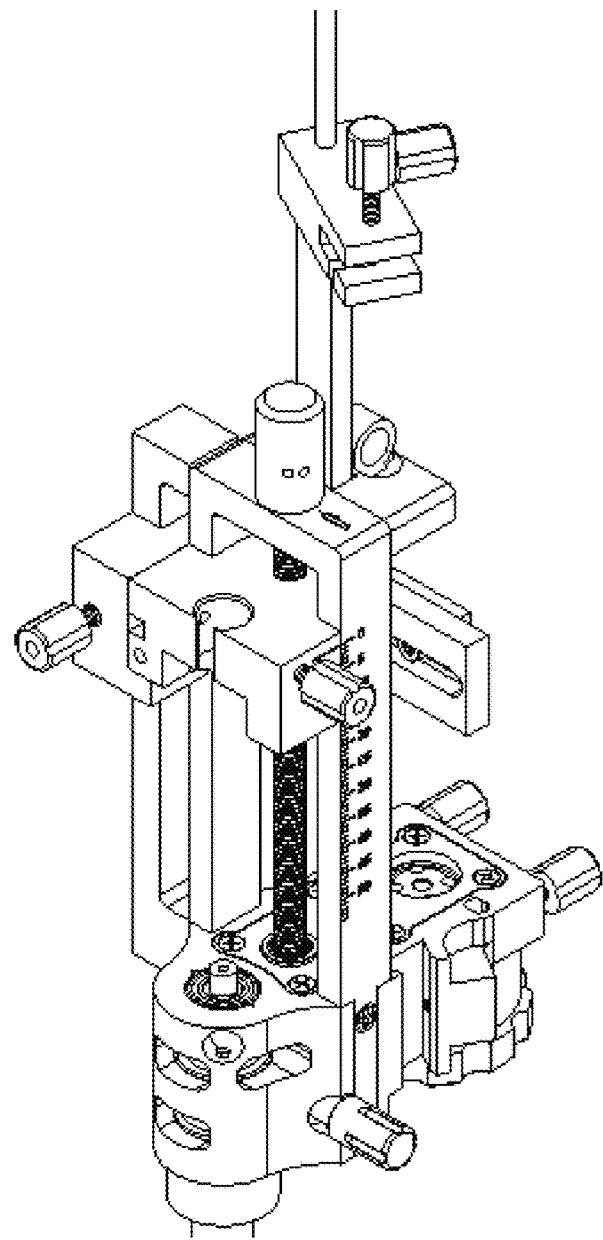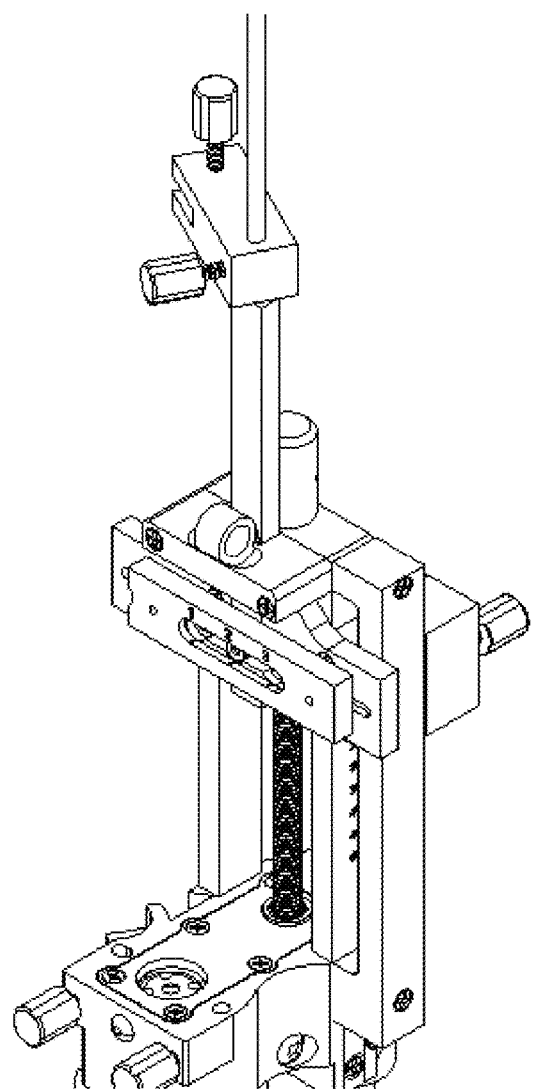
FIG. 8A
FIG. 8B

METHOD AND APPARATUS FOR CONTROLLED RELATIVE MOTION OF SURGICAL INSTRUMENTS AND COMPONENTS

CROSS-REFERENCE TO RELATED APPLICATIONS

The present application is a divisional application of U.S. patent application Ser. No. 16/275,654, filed Feb. 14, 2019, which claims priority to U.S. Provisional Patent Application No. 62/631,096, filed Feb. 15, 2018, the content of which are incorporated herein by reference in their entirety.

BACKGROUND OF THE INVENTION

Field of the Invention

Provided herein are devices, systems, and methods for controlled relative motion of surgical instruments and components.

In particular, provided herein are devices, systems, and methods for controlling relative delivery of a therapeutic substance during a surgical intervention.

Description of Related Art

Delivery of therapeutic substance during surgery can involve a number of different protocols, depending on the nature of the therapeutic substance. For example, delivery of a growth factor or other substance that promotes growth or regeneration of a tissue can typically be delivered in a bolus form. With regard to neurosurgery, a stereotactic procedure can involve formation of a burrhole in the skull, attachment of a stereotactic frame or other targeting device, advancement of a cannula, and bolus delivery of a growth factor, neuroprotective substance, or the like.

In contrast, other therapeutic substance benefit from a therapeutic distribution. An example of such substance includes cell-based therapies. In such circumstances, again in the example of neurosurgery, a stereotactic procedure can involve formation of a burrhole in the skull, attachment of a stereotactic frame or other targeting device, and advancement of a cannula. To provide the therapeutic distribution of the therapeutic substance, the cannula can be withdrawn from a target site, while the surgeon or technician manually depresses a syringe plunger to provide the therapeutic distribution. However, this is an uncontrolled process that often results in inconsistent volumes of the therapeutic substance being dispensed per unit of distance. In addition, the delivery cannula cannot be extracted at the slow, controlled rate necessary to reduce therapeutic reflux along the cannula trajectory.

Accordingly, the need exists in the art for devices, systems, and methods to provide accurate therapeutic distribution of a therapeutic substance.

SUMMARY OF THE INVENTION

To address the above-identified problem, provided herein is a device for controlling relative delivery of a therapeutic substance during a surgical intervention. The device includes a base, a frame having a proximal end and a distal end attached to the base, an injection subassembly, and a relative motion subassembly. The injection subassembly includes a syringe carriage configured to interface with the frame, to hold a syringe and to hold a delivery cannula, a plunger shaft having a proximal end and a distal end. The plunger shaft connected at its distal end to the frame, and an instrument clamp configured to interact with the plunger shaft. The relative motion subassembly includes a carriage plate, a drive plate, a lever plate having one or more openings and connected to the carriage plate and the drive plate, and a fastener connecting the lever plate to the plunger shaft through one of the one or more openings of the lever plate. In the device, the interaction of the fastener, the one or more openings of the lever plate, and the plunger shaft controls a rate of delivery of a therapeutic substance during withdrawal of a cannula.

Also provided herein is a system including a device as described herein, a syringe and a cannula received by the syringe carriage, and a frame adapter, connected to the base of the device and configured to connect the device to a stereotactic frame.

Further embodiments and aspects are provided in the following clauses:

Clause 1. A device for controlling relative delivery of a therapeutic during a surgical intervention, comprising: a base; a frame having a proximal end and a distal end attached to the base; an injection subassembly comprising: a syringe carriage configured to interface with the frame and to be moveable relative thereto, to hold a syringe, and to hold a delivery cannula; and a plunger shaft having a proximal end and a distal end, the plunger shaft connected at its distal end to the frame; and an instrument clamp configured to interact with the plunger shaft; a relative motion subassembly comprising: a carriage plate; a drive plate; and a lever plate comprising one or more openings and connected to the carriage plate and the drive plate; and a fastener connecting the lever plate to the plunger shaft through one of the one or more openings of the lever plate, wherein interaction of the fastener, the one or more openings of the lever plate, and the plunger shaft controls a rate of delivery of the therapeutic during withdrawal of a cannula.

Clause 2: The device according to clause 1, wherein the one or more openings in the lever plate correspond to one or more injection rates.

Clause 3: The device according to clause 1 or clause 2, wherein the one or more openings in the lever plate comprise an elongated opening with one or more seats for the fastener.

Clause 4: The device according to clause 3, wherein the one or more seats correspond to one or more injection rates.

Clause 5: The device according to any of clauses 1-4, wherein the injection subassembly further comprises a carriage connector comprising a fastener configured to releasably connect the carriage connector to the frame.

Clause 6: The device according to clause 5, wherein when the carriage connector is connected to the frame, the drive plate is held in place during withdrawal of the syringe carriage.

Clause 7. The device according to clause 5, further comprising one or more resiliently-biased members configured to resiliently bias the carriage connector against the syringe carriage while the carriage connector is not connected to the frame.

Clause 8: The device according to any of clauses 1-7, further comprising a fastener configured to releasably connect a syringe to the syringe carriage.

Clause 9: The device according to any of clauses 1-8, further comprising one or more fasteners configured to releasably connect a syringe plunger to the instrument clamp.

Clause 10: The device according to any of clauses 1-9, further comprising one or more fasteners configured to hold the instrument clamp at a relative location along the syringe plunger.

Clause 11: The device according to any of clauses 1-10, further comprising a motor or drive for advancing and withdrawing the syringe carriage along a longitudinal axis of the device.

Clause 12: A system comprising: the device of any of clauses 1-11; a syringe and a cannula received by the syringe carriage; and a frame adapter, connected to the base of the device and configured to connect the device to a stereotactic frame.

Clause 13: The system of clause 12, further comprising one or more computing devices.

Clause 14: The system of clause 13, wherein the computing devices control, through one or more motors or drives, one or more of: a rate of advancement of the cannula to a target site within a patient; and a rate of withdrawal of the cannula from the target site.

Clause 15: A system for controlling relative delivery of a therapeutic during a surgical intervention, comprising: a base; a frame having a proximal end and a distal end attached to the base; an injection subassembly comprising: a syringe carriage configured to interface with the frame and be moveable relative thereto, to hold a syringe and a delivery cannula; and a plunger shaft having a proximal end and a distal end, the plunger shaft connected at its distal end to the frame; and a syringe clamp configured to interact with the plunger shaft; and a syringe comprising a delivery cannula attached to a syringe body and a syringe plunger received within the syringe body, wherein, when the syringe plunger is secured to the syringe clamp, as the cannula is withdrawn from the target, the syringe plunger is held in place by the syringe clamp such that the syringe plunger moves at a ratio of relative to the syringe body at a ratio of 1:1 relative to movement of the cannula, to cause delivery of a therapeutic as the cannula is withdrawn.

BRIEF DESCRIPTION OF THE DRAWINGS

FIGS. 8A-8L show a series of steps in a method of using a device according to one non-limiting aspect of the invention described herein;

DESCRIPTION OF THE INVENTION

Figure 1:
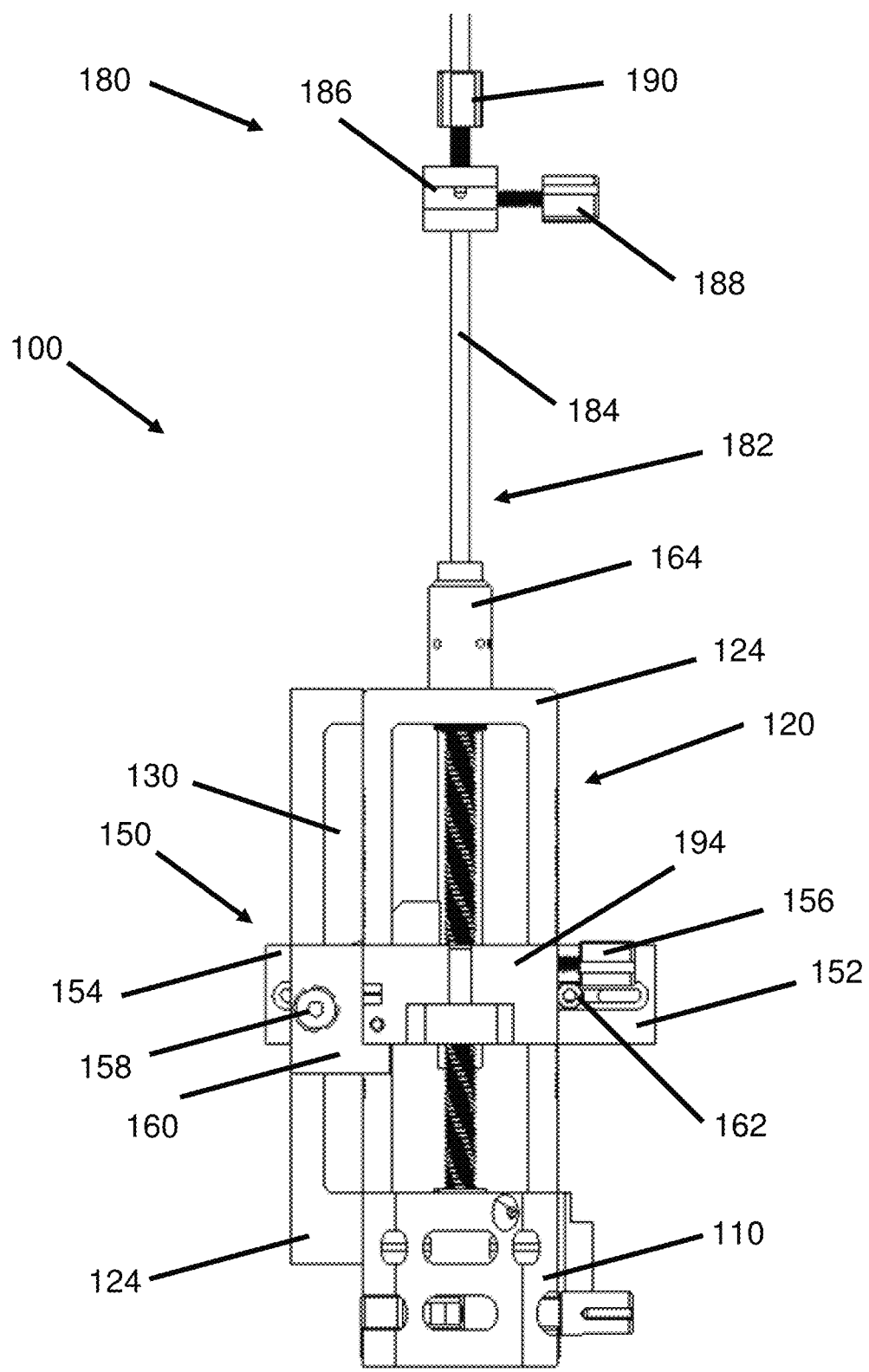
FIG. 1 shows a frontal view of a device according to one non-limiting aspect of the invention described herein.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

All references cited within this specification are incorporated by reference herein in their entirety.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention can assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The figures accompanying this application are representative in nature and should not be construed as implying any particular scale or directionality unless otherwise indicated.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein, "a" and "an" refer to one or more.

As used herein, the term "patient" refers to members of the animal kingdom including but not limited to mammals and human beings and is not limited to humans or animals in a doctor-patient or veterinarian-patient relationship. "A patient" refers to one or more patients such that a treatment effective in "a patient" refers to a treatment shown effective in one patient or a statistically significant number of patients in a population of patients.

Provided herein is a device for controlling relative delivery of a therapeutic substance during a surgical intervention. With reference to FIG. 1, shown is a non-limiting aspect of a device (100) as described herein. The device (100) includes a base (110), a frame (120), and an injection subassembly (180). Such a device can be utilized to deliver a therapeutic substance as a syringe is withdrawn. In some non-limiting aspects, the substance is delivered at a 1:1 ratio of movement between a syringe plunger and the withdrawal of the syringe from a target site. In some non-limiting aspects, the device (100) includes a relative motion subassembly (150) to allow for further refinement and adjustment of the rate of substance delivery during withdrawal. However, it should be appreciated by those of skill in the art that the relative motion subassembly (150) can be configured to provide the same 1:1 ratio of plunger movement to syringe withdrawal capable from a device without such a subassembly. In some non-limiting aspects, the base (110) can be configured, either itself or through attachment to one or more frame adapters, to connect to a stereotactic frame or other guidance fixture for guiding a surgical trajectory.

With continued reference to FIG. 1, while the frame (120) is shown having a rectangular arrangement, those of skill in the art will appreciate that the shape of the frame is not critical so long as the frame can be interconnected with an injection subassembly and a relative motion subassembly. Frame (120) includes a proximal end (122), a distal end (124), and a side portion or u-slot (130), which protrudes laterally from the frame (120). As with the shape of frame (120), the side portion (130) can be any useful shape, so long as it serves the purpose described below.

Frame (120) and side portion/u-slot (130) may be formed out of any suitable material that is considered biosafe and or suitable for use in a biomedical application, such as surgery.

With further reference to FIG. 1, device (100) includes an injection subassembly (180), which may include one or more of a syringe carriage (194), fasteners (156, 158), a carriage connector (160), a plunger shaft (184), an instrument clamp (186), and fasteners (188, 190). As above, these components may be formed out of any suitable material and may assume any useful shape. Plunger shaft (184) includes a proximal end and a distal end. The distal end may be attached to the frame (120). Instrument clamp (186) can be configured to attach, reversibly or irreversibly, to a proximal end of the plunger shaft (184), and thus, in aspects, can be a plunger holder. Instrument clamp (186) can also be configured to attach, reversibly or irreversibly, to a medical device or instrument. In certain non-limiting aspects, instrument clamp (186) is configured to attach to a plunger of a syringe (182). Through attachment to the frame (120) and, for example a syringe (182) plunger, plunger shaft (184) and instrument clamp (186) can actuate the syringe, causing the plunger to expel a therapeutic agent, as a cannula (192) is withdrawn from an injection or target site within a patient's body.

Syringe carriage (194) provides a location for a syringe (182) to be mounted to device (100). Syringe (182) can be connected, for example and without limitation through a press fit, friction fit, luer lock, or other removable or permanent fitting providing fluid communication therebetween, to a cannula (192). The cannula (192) is utilized to provide a path between the syringe (182) and the target area for delivery of a therapeutic substance. In non-limiting aspects, the device (100) can be used to withdraw a substance from a target site by reversing components described herein to allow for withdrawal of a syringe plunger.

Figure 4:
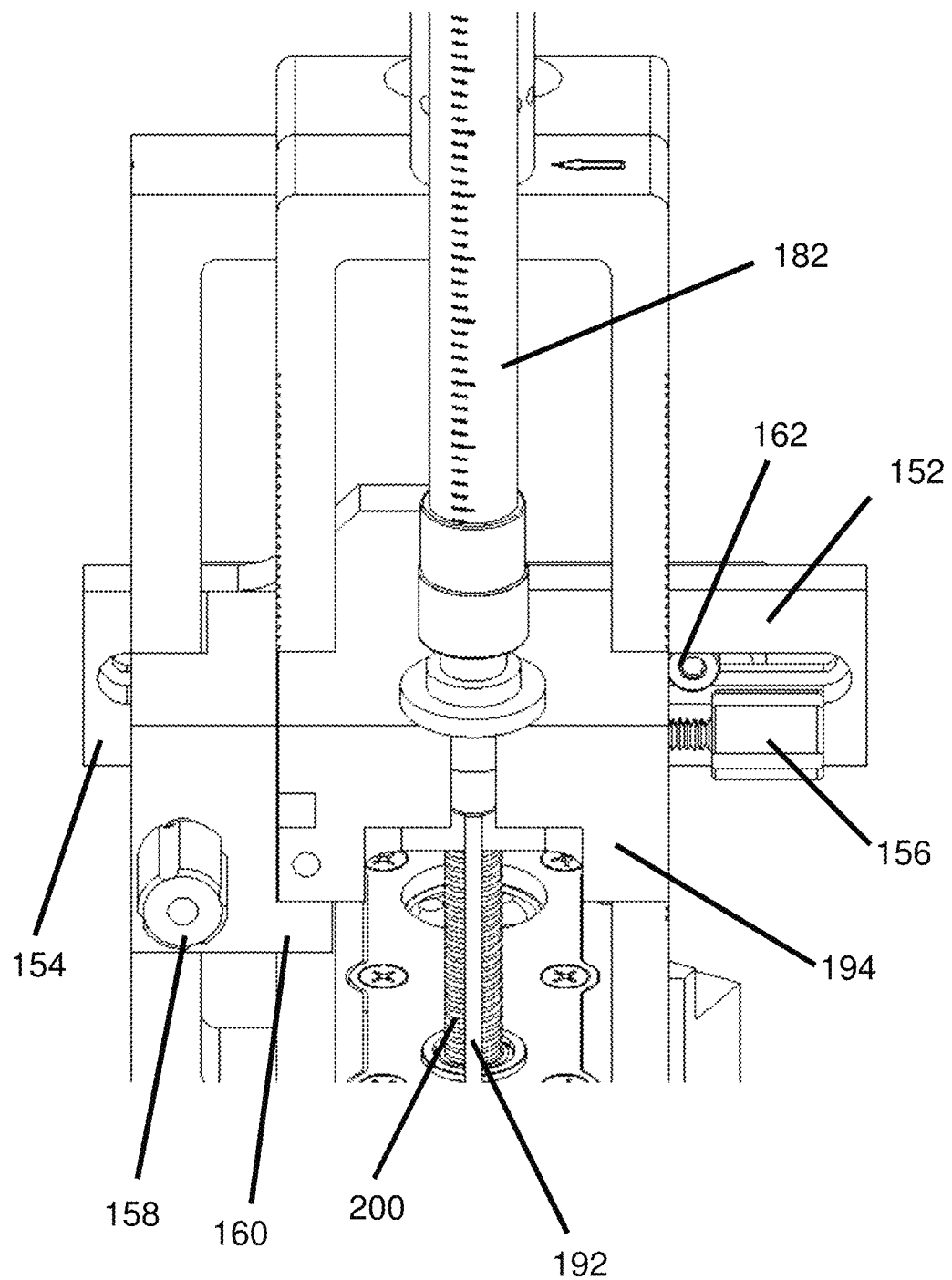
FIG. 4 shows a frontal view of a device according to one non-limiting aspect of the invention described herein.

With reference to FIG. 4, the syringe (182) can be secured to the syringe carriage (194) through fastener (156). Fastener (156) may be any suitable fastener that provides a reversible or irreversible attachment or coupling between the syringe carriage (194) and syringe (182). In non-limiting aspects, fastener (156) provides an interference fit, friction fit, and/or compression fit. In addition, syringe carriage (194) can be configured to provide a secure connection with syringe (182). For example, and without limitation, syringe carriage (194) can include a groove for receiving a portion of the syringe (182), and the groove can be sized or configured to allow a portion of the syringe (182) to snap, or be received in an interference or friction fit, with syringe carriage (194). Those of skill in the art will appreciate that any number of arrangements can be utilized, provided that the syringe (182) is secure to the moveable syringe carriage (194).

Syringe carriage (194) is moveable along a longitudinal axis of frame (120) through interaction with drive screw (200). For example, and without limitation, cooperative engagement between threads on or within a portion of syringe carriage (194) and threads of drive screw (200) allow for longitudinal movement to place cannula (192) at a proper depth within the patient's body, and allows for withdrawal of the cannula (192) and delivery of a therapeutic substance through interaction of the syringe (182) plunger with instrument clamp (186) and plunger shaft (184). The syringe carriage (194) is fixed in orientation by the frame (120), but not constrained in lateral movement. The drive screw (200) is held in place by bearings (not shown) which permit rotation along the screw axis, but which restrict displacement along the screw axis. The thread engagement between the drive screw (200) and syringe carriage (194) allows the syringe carriage (194) to be moved along the drive screw axis when the drive screw (200) is rotated.

Figure 6:
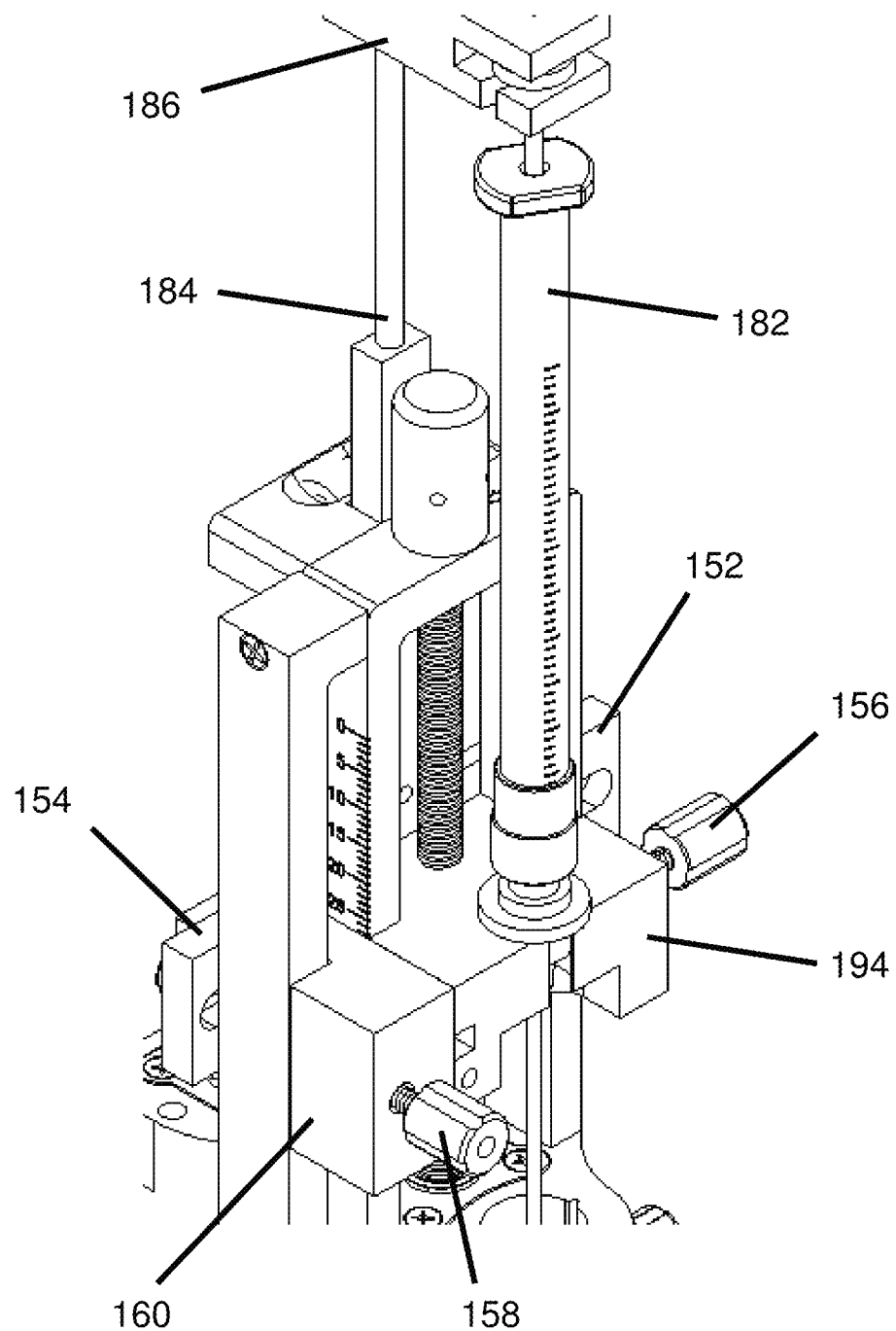
FIG. 6 shows a perspective view of a device according to one non-limiting aspect of the invention described herein.

With continued reference to FIG. 1, carriage connector (160) is a separately lockable component of the injection subassembly (180). Carriage connector (160) travels longitudinally with the syringe carriage during insertion of cannula (192) prior to delivery of a therapeutic substance. With reference to FIG. 6, when cannula (192) has reached the desired depth or penetration, fastener (158) is utilized to lock carriage connector (160) to the frame (120). Fastener (158) may be any suitable fastener that provides a reversible or irreversible attachment or coupling between carriage connector (160) and frame (120), in particular aspects side portion/u-slot (130).

Figure 5:
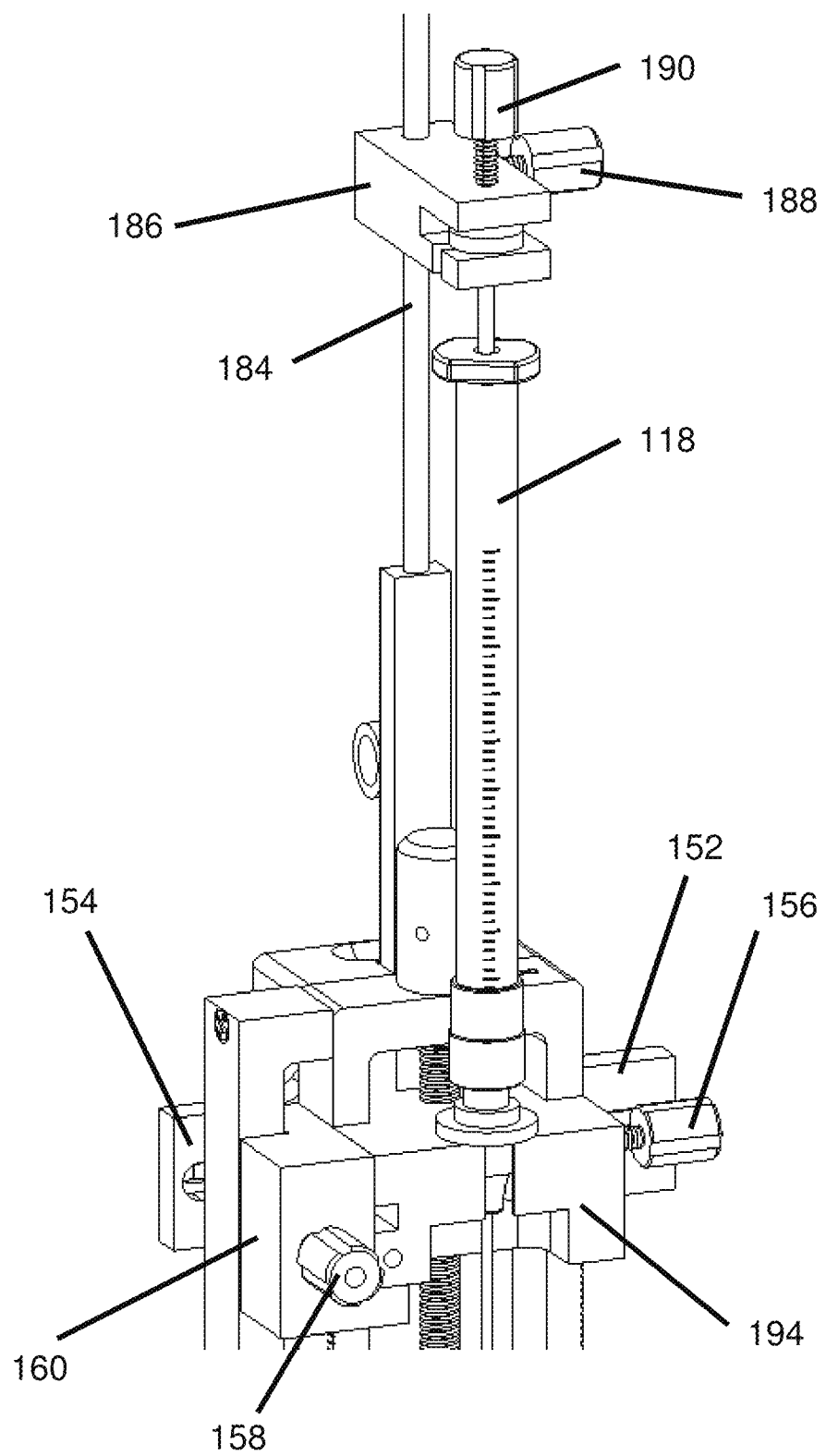
FIG. 5 shows a perspective view of a device according to one non-limiting aspect of the invention described herein.

Fasteners (188, 190) may be any suitable fastener that provides a reversible or irreversible attachment or coupling between instrument clamp (186) and plunger shaft (184), and between instrument clamp (186) and an instrument, for example a syringe (182) plunger, utilized with device (100). With reference to FIG. 5, for example, and without limitation, fasteners (188, 190) can be screws, including thumb screws, and can provide, for example and without limitation, an interference fit, friction fit, or compression fit. For example, and without limitation, as shown in FIG. 5, fasteners (188, 190) can be thumb screws that provide a compressive fit, locking a syringe (182) plunger into the instrument clamp (186), and that lock the instrument clamp (186) to a particular location along a longitudinal axis of the plunger shaft (184).

Figure 2:
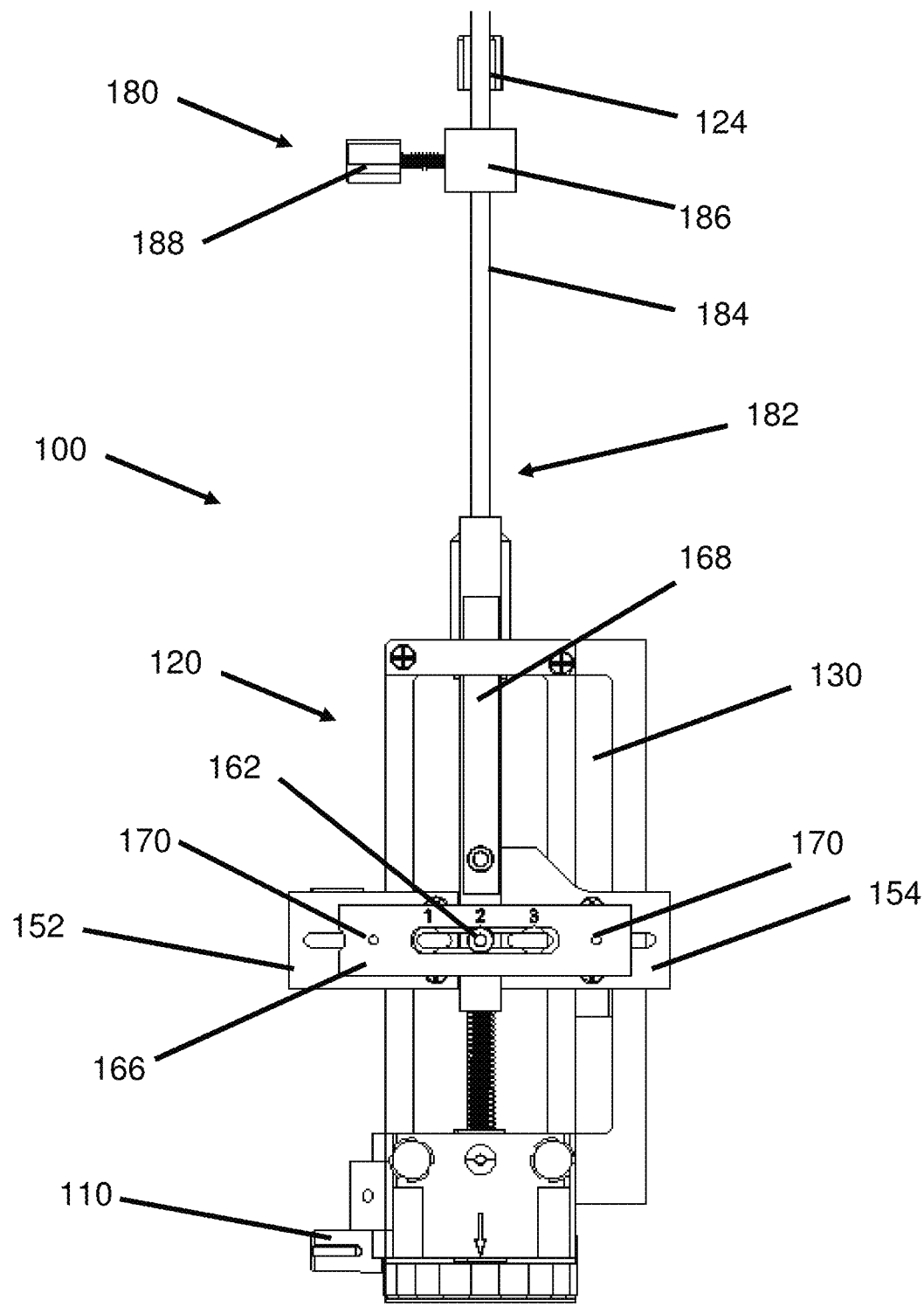
FIG. 2 shows a back view of a device according to one non-limiting aspect of the invention described herein.

With reference to FIG. 2, shown is a view of the back of a device (100) according to aspects of the present invention. In this view, a ribbon spring (168), which is a component of the injection subassembly (180), is visible. Ribbon spring (168) maintains the syringe carriage (194) in contact with carriage connector (160) during insertion of cannula (192).

Further to the above, in non-limiting aspects, as described previously, a syringe can be connected to the device (100) and used, with or without relative motion subassembly (150, described below), to deliver a therapeutic at a ratio of 1:1 (movement of the plunger relative to syringe body:syringe withdrawal) by locking a plunger shaft to instrument clamp (186) and withdrawing syringe (via syringe carriage (194)).

Also shown in FIG. 2 is relative motion/linkage subassembly (150), which can provide relative motion between cannula (192) withdrawal and syringe (182) actuation to provide a therapeutic distribution of a therapeutic substance at a range of ratios of plunger movement (relative to syringe body) and syringe withdrawal. Relative motion subassembly (150) can include carriage plate (152), drive plate (154), fastener (162) (which can be a pivot/rotation point), pivot or rotation point(s) (170) (which can be pivot/rotation points provided by fasteners), lever plate (166), and drive cap (164). The drive cap (164) accepts a proximal end of drive screw (200), allowing the drive screw (200) to be rotated by rotating the drive cap (164). This rotation allows movement of the syringe carriage (194). As above, these components may be formed out of any suitable material and may assume any useful shape.

In some non-limiting aspects, the relative motion subassembly aids in providing a desired injection rate for a therapeutic distribution of a substance. In general, injection rate is dependent on the type of syringe (182) that is used, the movement ratio of the relative motion subassembly (150), and the movement speed of the syringe carriage (194). The base injection rate is defined as the volume that the syringe (182) dispenses per distance that the plunger travels relative to the body of the syringe (182). While any suitable syringe may be used, in non-limiting aspects the device (100) is used with a 1725 Hamilton Syringe (Hamilton Robotics, Reno, NV). The modified injection rate is achieved by controlling the motion of the syringe (182) plunger relative to the syringe (182) base, which is mounted on the syringe carriage (194). The modified injection rate is a ratio of the volume dispensed per distance traveled by the syringe carriage (194) (i.e., the needle tip). The speed at which the syringe carriage (194) moves determines the injection rate as a ratio of volume dispensed per time.

Figure 3:
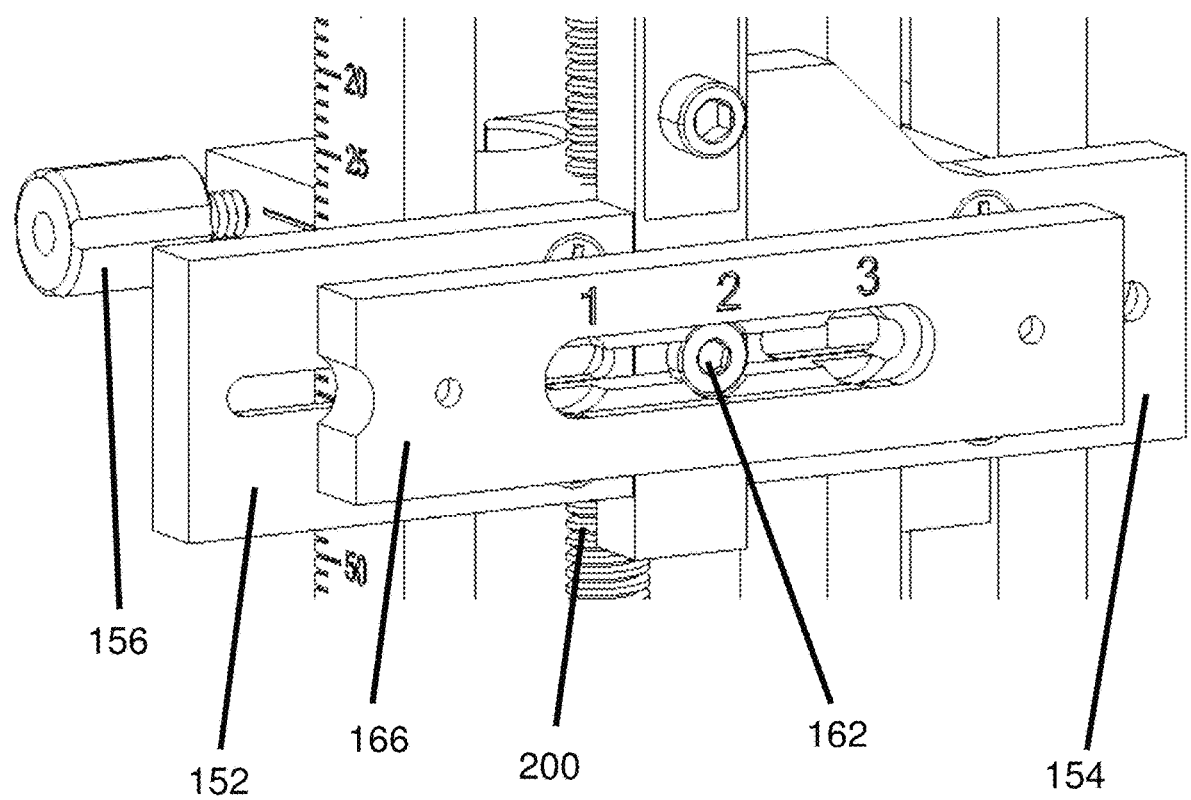
FIG. 3 shows a perspective view of a device according to one non-limiting aspect of the invention described herein.

With reference to FIG. 3, shown is the relative motion subassembly (150), including opening(s) that allow for fastener (162) to reversibly or irreversibly connect the relative motion subassembly (150), in particular aspects of the lever plate (166) of the subassembly, to the plunger shaft (184). In certain aspects, the lever plate (166) is oriented such that a circular cutout on one end is positioned to the left (i.e., the same side as the carriage plate (152)), as shown in FIG. 3. Lever plate (166) includes one or more openings in which fastener (162) can be received. Lever plate (166) can include indicia providing an indication of modified injection rate, depending on the position in which fastener (162) is seated. In some aspects, in addition to one or more openings in lever plate (166), seats may be provided into which fastener (162) may rest.

To change injection rate in the aspect shown in FIG. 3, fastener (162) that connects the plunger shaft (184) and the lever plate (166) together can be loosened. Once the screw has been loosened, the lever plate (166) can be moved to the desired hole/seat, and the fastener (162) can be tightened to provide a connection between the lever plate (166) and the plunger shaft (184). While the aspect of FIG. 3 exemplifies a screw that can be loosened and tightened, those of skill in the art will appreciate that any type of fastener can be used, so long as it is capable of allowing adjustment of the lever plate (166).

With regard to the modified injection rates described above, Table 1 below provides exemplary parameters and injection rates achievable with the device (100) described herein, when used with a STar™ Drive (FHC, Inc., Bowdoin, ME). The final injection rates listed are ratios per time, whereas other ratios are per distance. Specifically, with references to the below table, the column/value "Syringe Mounted on STar Drive" is a ratio of volume/distance (i.e. no specification has been made regarding the drive movement speed). Projecting that ratio given a drive speed setting ("FHC Motor/Controller" column) produces the ratio of volume/time in the column "Syringe Mounted on STar Drive w/Motor/Controller".

TABLE 1

| | Device | | | |
|---|---|---|---|---|
| | 1700 Series Hamilton Syringe | | FHC STar Drive M/E w/Present Invention | Syringe Mounted on STar Drive |
| | | | Constant | |
| | Volume (μL) | Scale Length (mm) | Base Injection Rate (Volume/Plunger Travel) (μL/mm) | Movement Ratio (Plunger Holder/Carriage) | Modified Injection Rate (Volume/Carriage Travel) (μL/mm) |
| | | | Description | | |
| | Total volume of syringe | Total length of scale on syringe | Volume injected by syringe per distance the plunger is advanced | Ratio of the movement of the plunger holder to the movement of the carriage (where the syringe base is mounted). | Volume injected by distance the carriage is retracted. Calculation (Base Injection Rate*Movement Ratio) |
| 1710 | 100.00 | 60.00 | 1.667 | 0.480 | 0.80 |
| | | | | 0.720 | 1.20 |
| 1725 | 250.00 | 60.00 | 4.167 | 0.480 | 2.00 |
| | | | | 0.720 | 3.00 |
| 1750 | 500.00 | 60.00 | 8.333 | 0.480 | 4.00 |
| | | | | 0.720 | 6.00 |

| Device | | |
|---|---|---|
| FHC Motor/Controller | | Syringe Mounted on STar Drive w/ Motor/Controller |
| | Constant | |
| Speed setting (μm/s) | Speed setting (mm/min) | Time Injection Rate (Volume/Time) (μL/min) |

TABLE 1-continued

| | Programmed speed the carriage will be retracted at | | Volume injected per time. Calculation (Modified Injection Rate*Speed) |
|---|---|---|---|
| 1710 | 42.00 | 2.52 | 2.02 |
| | 28.00 | 1.68 | 2.02 |
| 1725 | 17.00 | 1.02 | 2.04 |
| | 11.00 | 0.66 | 1.98 |
| 1750 | 8.50 | 0.51 | 2.04 |
| | 5.50 | 0.33 | 1.98 |

The movement ratio between the syringe carriage (194) and the instrument clamp (186) is controlled by the relative location of the fasteners and pivot points on the lever plate (166). Specifically, the relationship between the spacing of the two pivot points (170) and the location of the fastener (162) defines the movement ratio.

Figure 7:
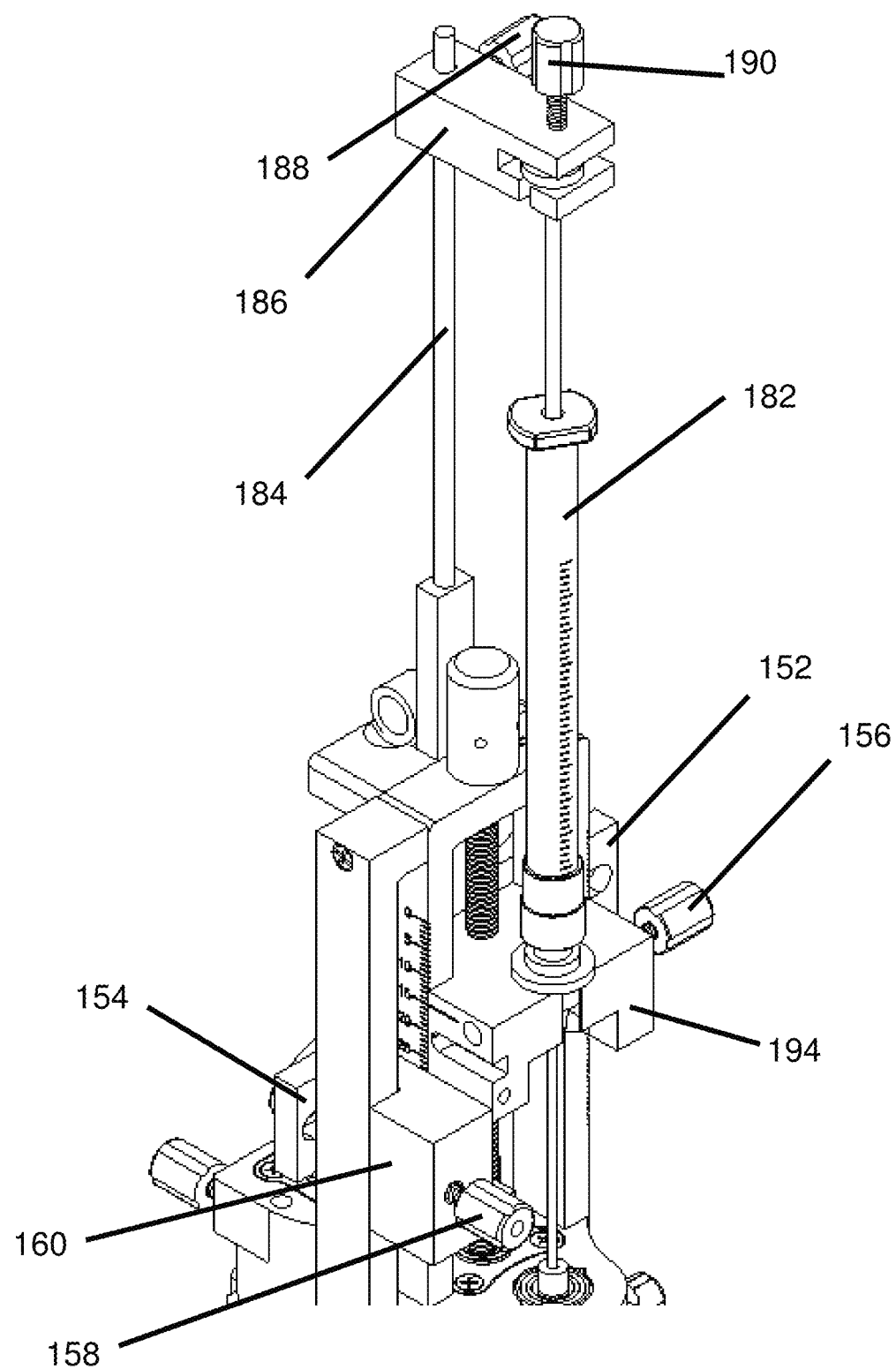
FIG. 7 shows a perspective view of a device according to one non-limiting aspect of the invention described herein.

Lever plate (166) can be attached or otherwise connected to, for example, rotatably connected to, carriage plate (152) and drive plate (154) via one or more pivot or rotation points (170) which are free to move latitudinally in the horizontal slots in the drive and carriage plates. The ability to pivot or rotate can be provided by any connection between the three plates that allows for rotation or pivoting of the lever plate (166) in relation to the carriage plate (152) and the drive plate (154). Carriage plate (152) can be connected to carriage connector (160), such that when carriage connector (160) is connected to frame (120), in some aspects side portion/u-slot (130) through fastener (158), drive plate (154) can be secured and locked in place longitudinally, and can no longer move longitudinally. This is shown in, for example, FIG. 7, which shows a front view of the carriage connector (160) secured to side portion/u-slot (130), while syringe carriage (194) is able to move proximally along a longitudinal axis. As the carriage plate (152) moves proximally with the drive plate (154) secured to the frame (120), the lever plate (166), which is connected to plunger shaft (184) can rotate about the fastener (162) and the pivot points (170) are free to move horizontally. As the carriage plate moves longitudinally and the drive plate remains stationary, the plunger shaft moves longitudinally at a different rate due to the fixed distances between the pivot points (170) and fastener (162). Since the lever plate (166) is a rigid body, when the vertical distance between the pivot points (170) increases, the vertical distance between the fastener (162) and drive plate pivot point (170) increases, but not as much. This results in the plunger shaft (184) moving longitudinally at a slower rate than the carriage (194) causing an injection of the syringe contents while the syringe tip is retracted.

Also provided herein is a system for providing a controlled rate of delivery of a therapeutic substance during a surgical intervention. The system may include device (100) described above and illustrated in various aspects in FIGS. 1-7. In addition, the system can include a syringe (182), cannula (192), adapter to connect frame (120) to a stereotactic or other targeting apparatus, and one or more computing devices to control the insertion and targeting of cannula (192) and withdrawal of cannula (192) with therapeutic distribution provided by syringe (182) and relative motion thereof in relation to the cannula withdrawal.

A computer, or computing system, capable of being used with the system described herein may include, but is not limited to, at least one computer having certain components for appropriate operation, execution of code, and creation and communication of data. For example, the computer includes a processing unit (typically referred to as a central processing unit or CPU) that serves to execute computer-based instructions received in the appropriate data form and format. Further, this processing unit may be in the form of multiple processors executing code in series, in parallel, or in any other manner for appropriate implementation of the computer-based instructions.

The computer further includes a system memory with computer storage media in the form of volatile and non-volatile memory, such as ROM and RAM. A basic input/output system (BIOS), with appropriate computer-based routines, assists in transferring information between components within the computer and is normally stored in ROM. The RAM portion of the system memory typically contains data and program modules that are immediately accessible to or presently being operated on by processing unit, e.g., an operating system, application programming interfaces, application programs, program modules, program data, and other instruction-based computer-readable codes.

A user may enter commands, information, and data into the computer through certain attachable or operable input devices, such as a keyboard, a mouse, etc., via a user input interface. A variety of such input devices may be utilized, e.g., a microphone, a trackball, a joystick, a touchpad, a touch-screen, a scanner, etc., including any arrangement that facilitates the input of data, and information to the computer from an outside source. As discussed, these and other input devices are often connected to the processing unit through the user input interface coupled to the system bus, but may be connected by other interface and bus structures, such as a parallel port, game port, or a universal serial bus (USB). Still further, data and information can be presented or provided to a user in an intelligible form or format through certain output devices, such as a monitor (to visually display this information and data in electronic form), a printer (to physically display this information and data in print form), a speaker (to audibly present this information and data in audible form), etc. All of these devices are in communication with the computer through an output interface coupled to a system bus. It is envisioned that any such peripheral output devices may be used to provide information and data to the user.

The computer may operate in a network environment through the use of a communications device, which is integral to the computer or remote therefrom. This communications device is operable by and in communication with the other components of the computer through a communications interface. Using such an arrangement, the computer may connect with or otherwise communicate with one or more remote computers, such as a remote computer, which may be a personal computer, a server, a router, a network personal computer, a peer device, or other common network nodes, and typically includes many or all of the components described above in connection with the computer. Using appropriate communication devices, e.g., a modem, a network interface or adapter, etc., the computer may operate within and communicate through a local area network (LAN) and a wide area network (WAN), but may also include other networks, such as a virtual private network (VPN), an office network, an enterprise network, an intranet, the Internet, etc. It will be appreciated that the network connections shown are exemplary and other means of establishing a communications link between the computers may be used.

As used herein, the computer includes or is operable to execute appropriate custom-designed or conventional software to perform and implement the processing steps of the method and system of the present invention, thereby forming a specialized and particular computing system. Accordingly, the system and method described herein may include one or more computers or similar computing devices having a computer-readable storage medium capable of storing computer-readable program code or instructions that causes the processing unit to execute, configure, or otherwise implement the methods, processes, and transformational data manipulations discussed hereinafter in connection with the present invention. Still further, the computer may be in the form of a personal computer, a personal digital assistant, a portable computer, a laptop, a palmtop, a mobile device, wearable technology such as a smart watch or other smart accessory, a mobile telephone, a server, or any other type of computing device having the necessary processing hardware to appropriately process data to effectively implement the system and method described herein.

It will be apparent to one skilled in the relevant art that the system may utilize databases physically located on one or more computers which may or may not be the same as their respective servers. For example, programming software on a computer can control a database physically stored on a separate processor of the network or otherwise.

A drive or driving element, for example, the controlling drive screw (200) of the device (100), can be in communication with one or more processors. As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication can use a direct or indirect connection and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11 and other radio frequency-based protocols and methods), analog transmissions, Global System for Mobile Communications (GSM), and/or the like.

A computing system as described above can be used to control the advancement of the cannula (192), and subsequent withdrawal (together with delivery of the therapeutic substance through syringe (182)). For example, the computing system can include a processor and non-transitory, computer-readable media containing programming instructions that, when executed by the processor, cause the processor to control movement of any component of device (100). The computing system can also include memory to allow for calculation of injection rate based on the identity (manufacturer, size, gauge, etc.) of syringe (182) and cannula (192), the arrangement of the lever plate (166), and speed of any motor/drive in moving syringe carriage (194). For example, and without limitation, the computing system memory can include a "lookup" chart or database with data of various manufacturers, syringe/cannula gauges (bore sizes), various therapeutic substances (including, without limitation, viscosity of the substance, and possible/preferred therapeutic distributions and/or delivery or injection rates), and the effect of the various positions of the lever plate (166) (i.e., the location along the one or more openings in the lever plate (166) where the fastener (162) is seated). Based on information that is entered into computing system, either by a user (i.e, a surgeon or technician), or that is entered by way of a sensor for scanning indicia (such as machine-readable indicia) included on one or more components of the device (100), the processor can calculate the possible and/or optimal injection rates, identify to the user the positioning of the fastener (162) in lever plate (166), and/or control a drive or motor to cause movement of the syringe carriage (194) as a specific speed or range of speeds across a specific distance.

The above information can be utilized, with an algorithm, for example, to calculate the injection volume, distance injected or ratio, given the other variables. The equation below shows the relationship:

$$V = d(\text{Syringe Base Rate}_{per\ distance})(\text{Relative Ratio})$$

Generally, the Syringe Base Rate will be a fixed constant, dependent upon which syringe is used, and the relative ratio will have discrete settings based on the lever plate screw setting. In aspects, the lever plate can be configured to allow continuous settings, rather than discrete seats. However, a custom lever plate could be created to achieve a desired distance and volume combination. Using this equation, a user could input the syringe type and relative ratio, then select a desired injection volume, and the required injection distance can be calculated. Drive/motor speed is an independent setting and can be controlled without affecting the variables previously listed which allows the user to optimize based on the therapeutic substance.

Figures 8C, 8D:
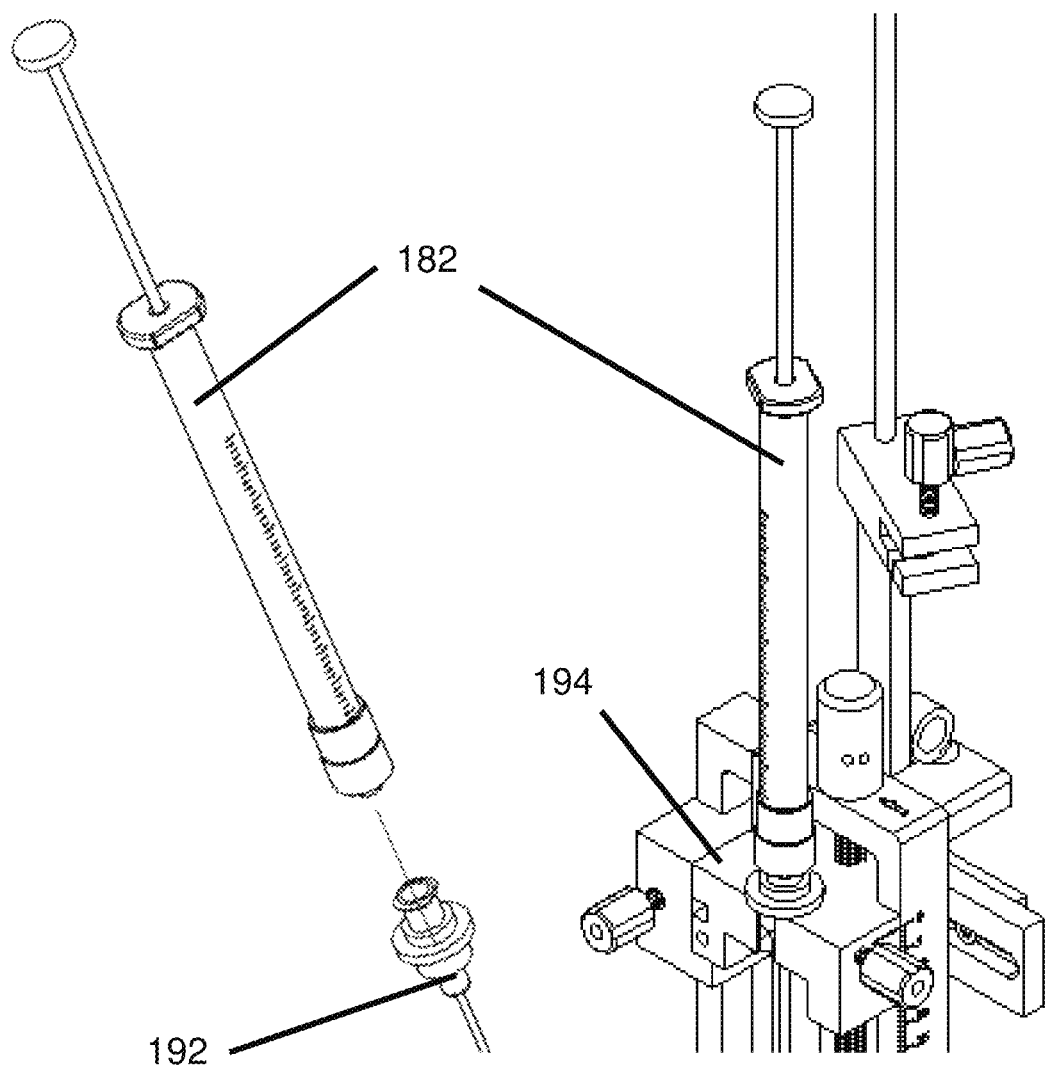

Also provided herein is a method of delivering a therapeutic substance to a patient using a device or system as described herein. An exemplary method is shown in FIGS. 8 and 9. A device (100) as described above can be attached to a targeting frame or other targeting device, at the site of a surgical intervention, for example through one or more frame adapters. FIGS. 8A and 8B show the device (100) without a syringe attached. Based on information described above (i.e., syringe manufacturer and/or size, therapeutic substance, and desired injection rate), a computing system can provide, or a user can look up, the proper positioning of the lever plate (166) in relation to the fastener (162). Lever plate (166) can then be secured at the identified location (i.e., fastener (162) can be seated at the desired portion of the one or more openings). As shown in FIG. 8C, syringe (182) containing the therapeutic substance can then be attached to cannula (192), through a luer connection or any other suitable type of fluid connection for medical devices. As shown in FIG. 8D, syringe (182) and cannula (192) can then be seated on syringe carriage (194). As described above, syringe (182), and/or cannula (192) can be secure to syringe carriage (194) through fastener (156), an interference or friction fit between syringe (182) and/or cannula (192) and syringe carriage (194), or any combination thereof.

Figures 8E, 8F:
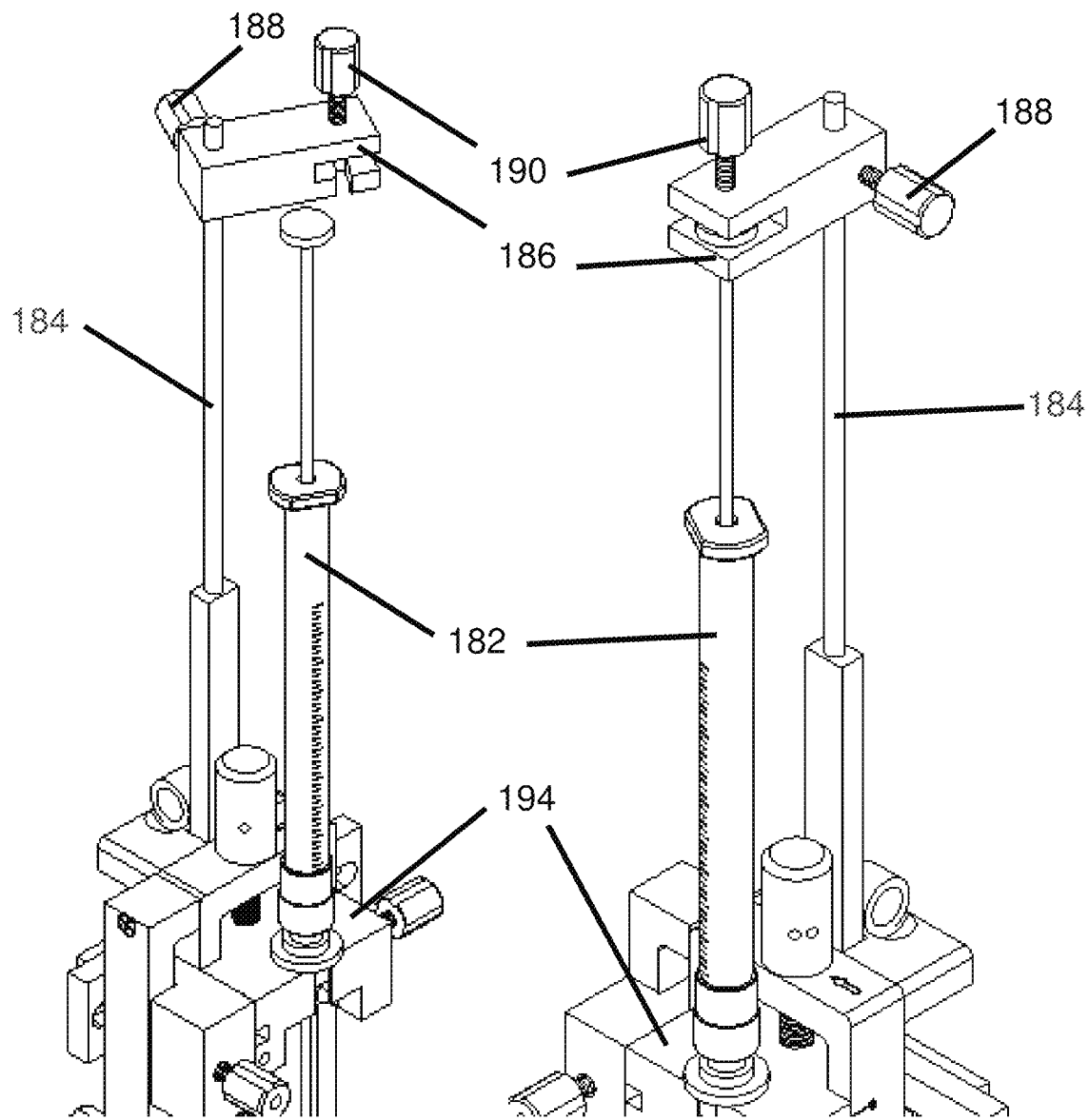
Figure 8G:
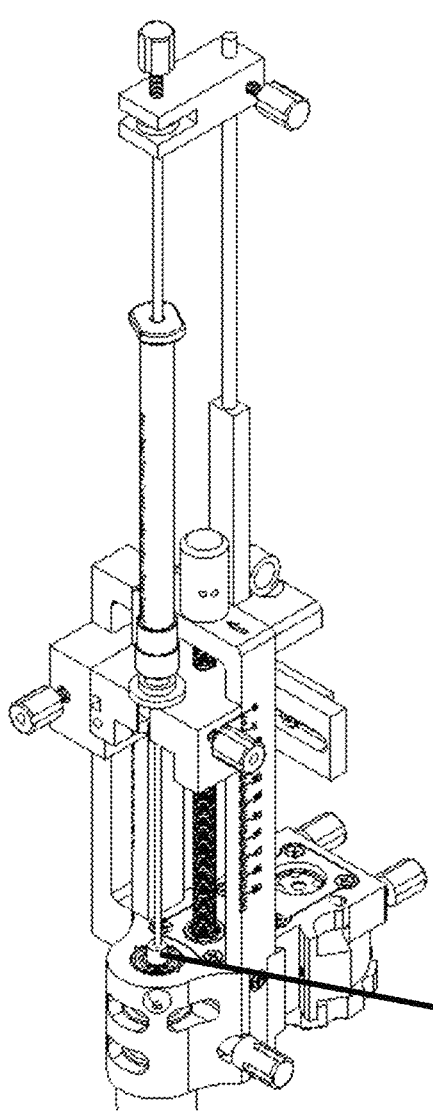
Figure 9:
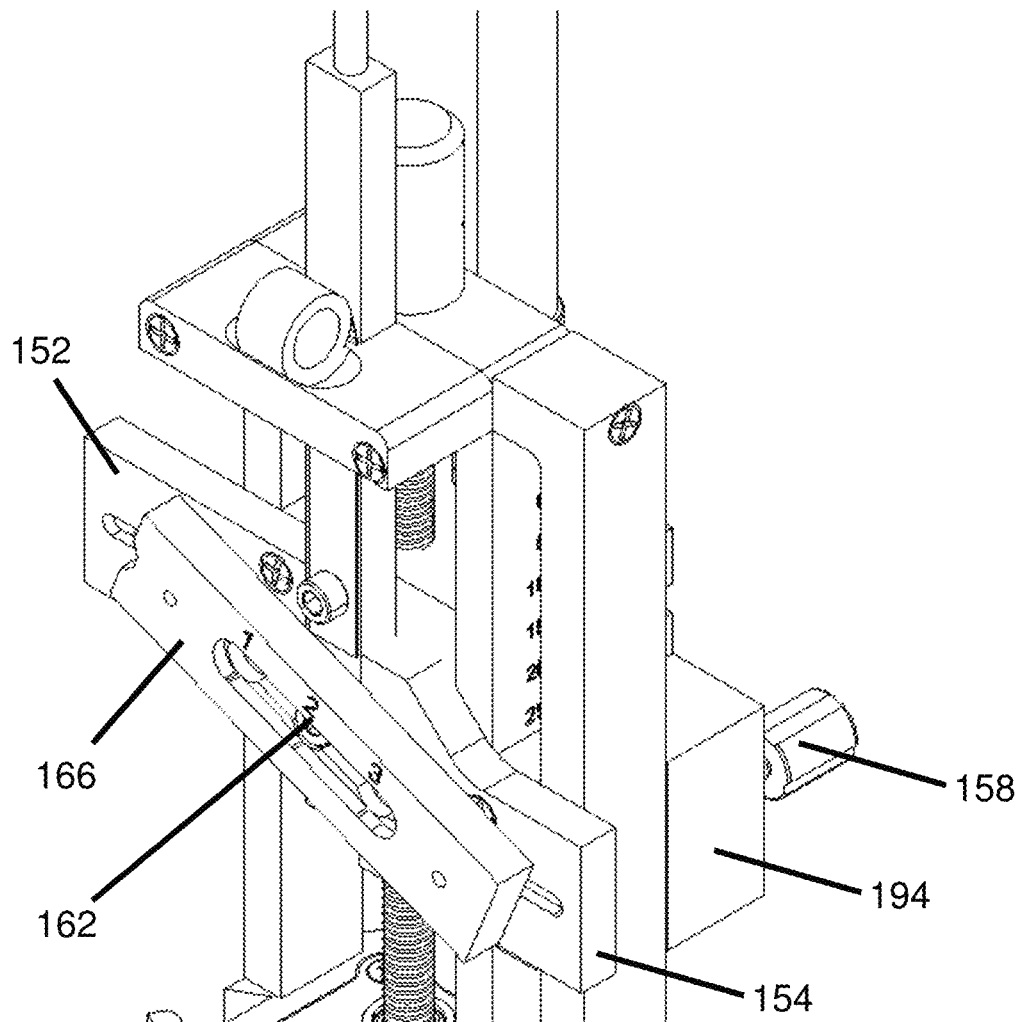
FIG. 9 shows an enlarged view of a step of the method of FIGS. 8A-8L according to one non-limiting aspect of the invention described herein.
Figure 10:
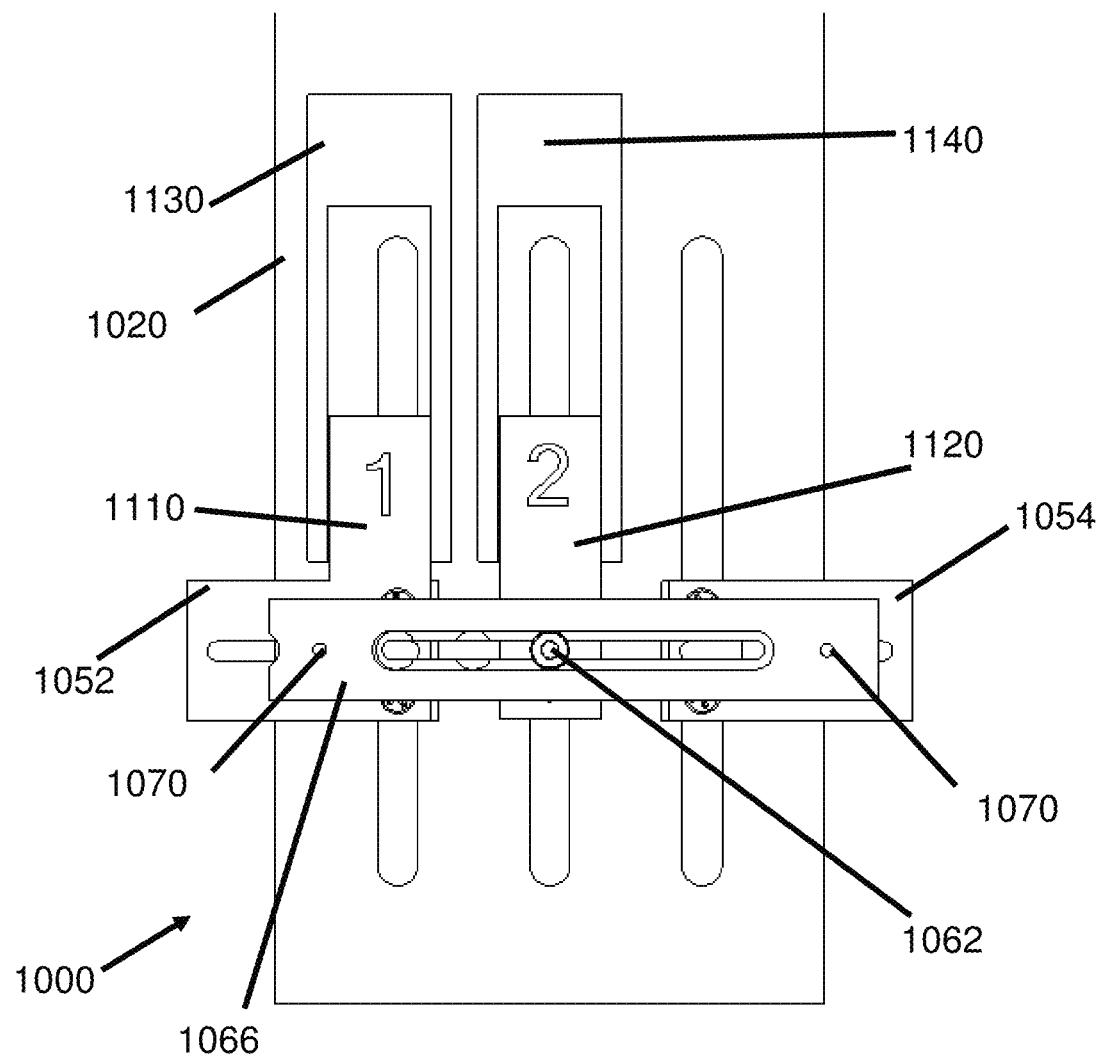
FIG. 10 shows a back view of a device according to one non-limiting aspect of the invention described herein.
Figure 11:
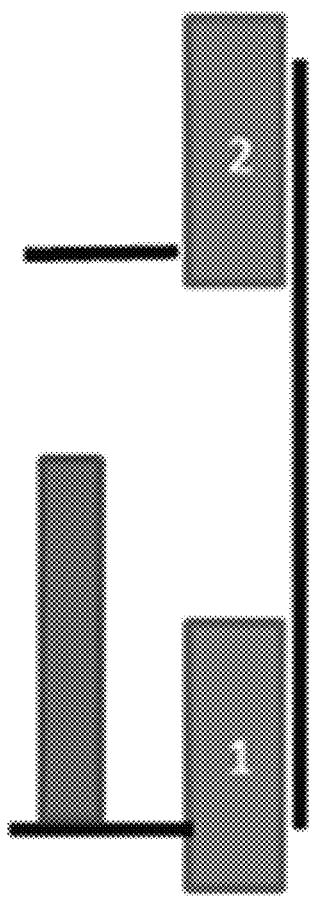
FIG. 11 shows a schematic of a device according to one non-limiting aspect of the invention described herein.
Figure 12:
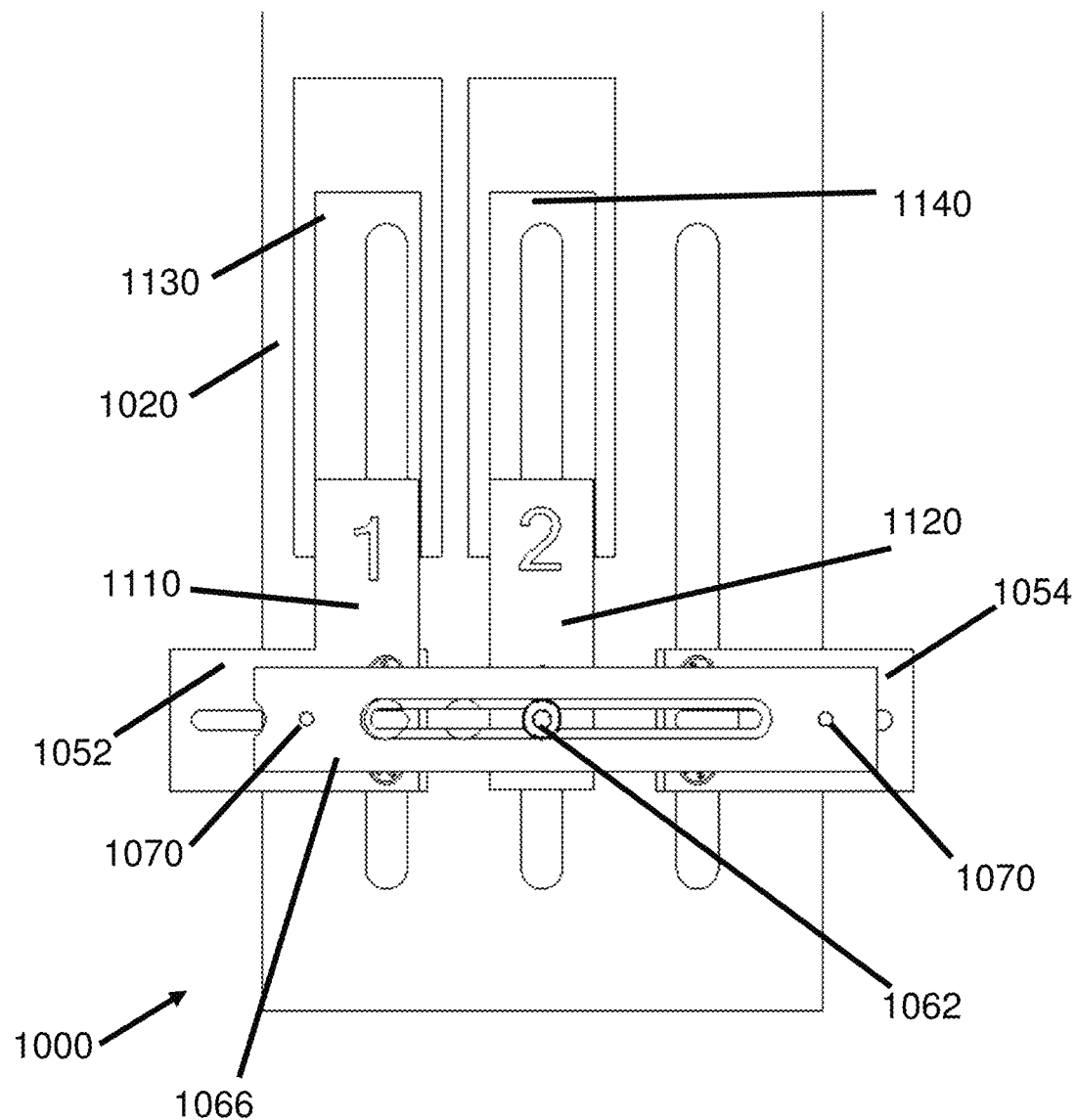
FIG. 12 shows a back view of a device according to one non-limiting aspect of the invention described herein.

Once syringe (182) and cannula (192) are seated on syringe carriage (194), as shown in FIGS. 8E-8F, instrument clamp (186) can be adjusted to interact with syringe (182) plunger, and the instrument clamp can be secured to the plunger shaft (184) and secured to the syringe (182) plunger as described above (i.e., through use of fasteners (188) and (190), respectively). Once syringe (182) is fully secured on syringe carriage (194) and instrument clamp (186), as shown in FIG. 8G, drive/motor, in some aspects as controlled by a computing system as described above, can cause the cannula (192) to move to the target site with the patient's body.

Figure 8H:
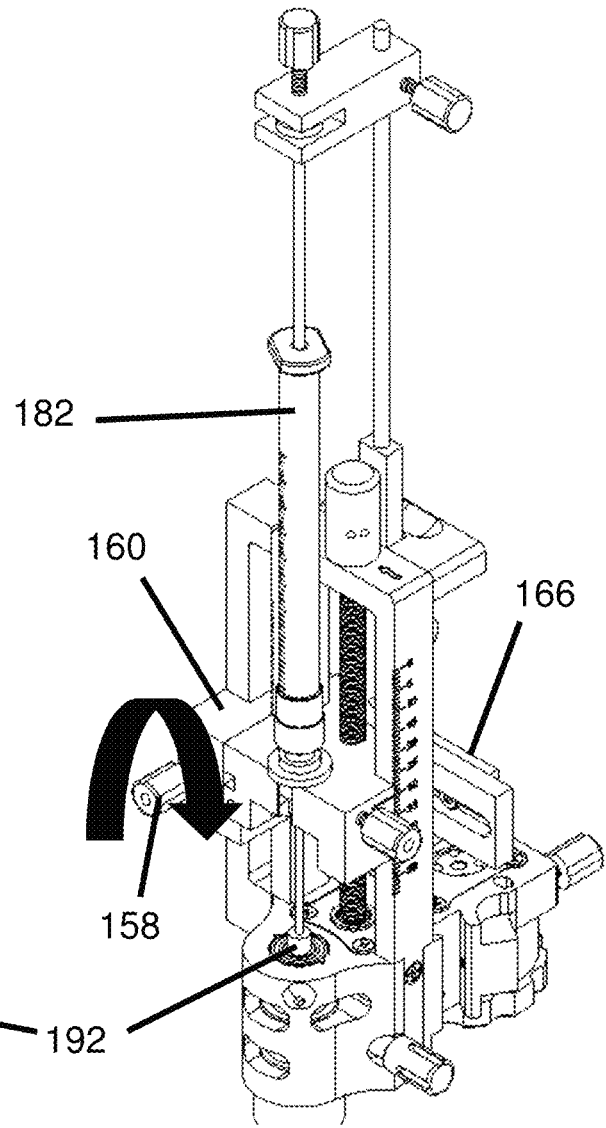
Figures 8I, 8J:
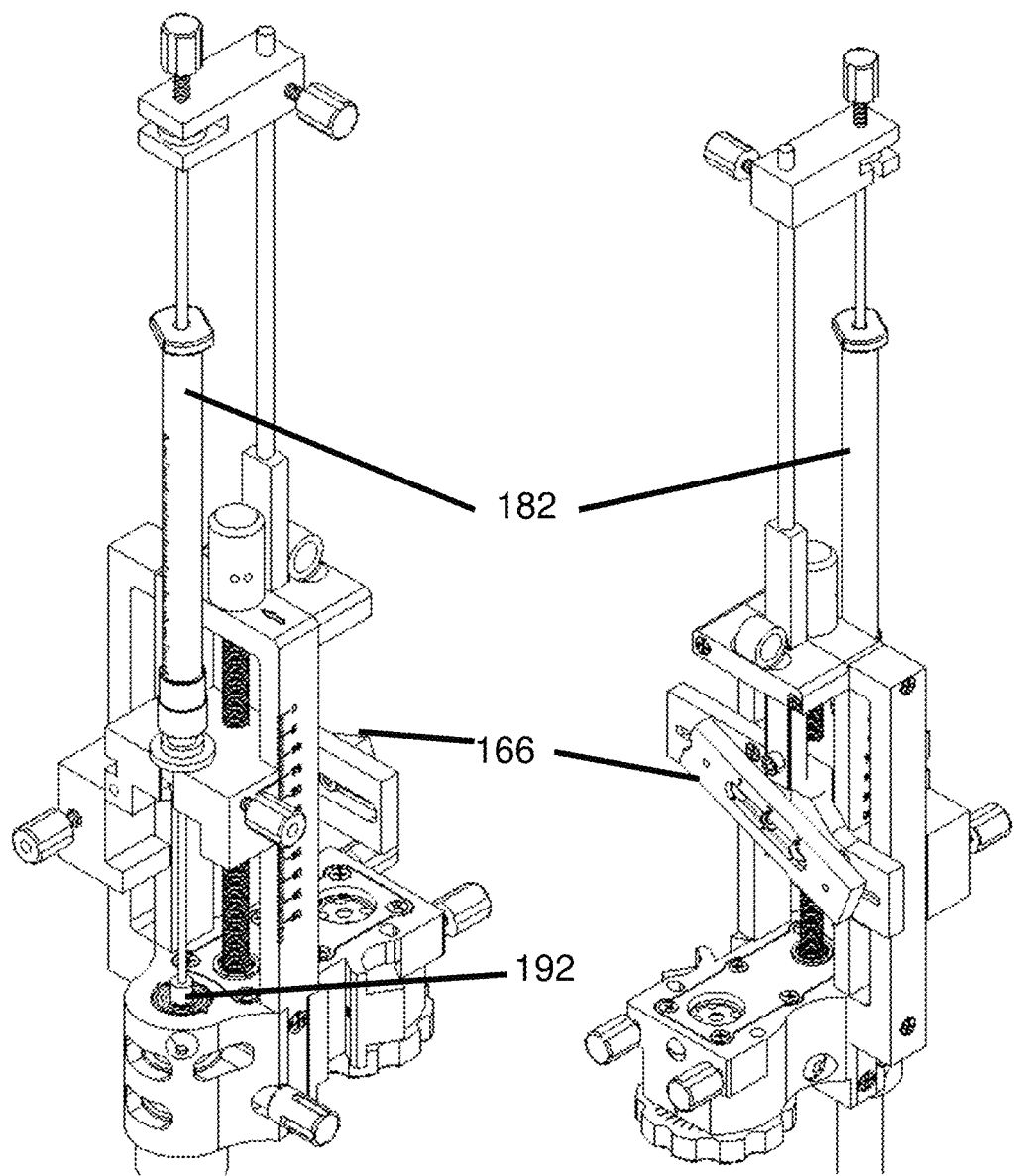
Figures 8K, 8L:
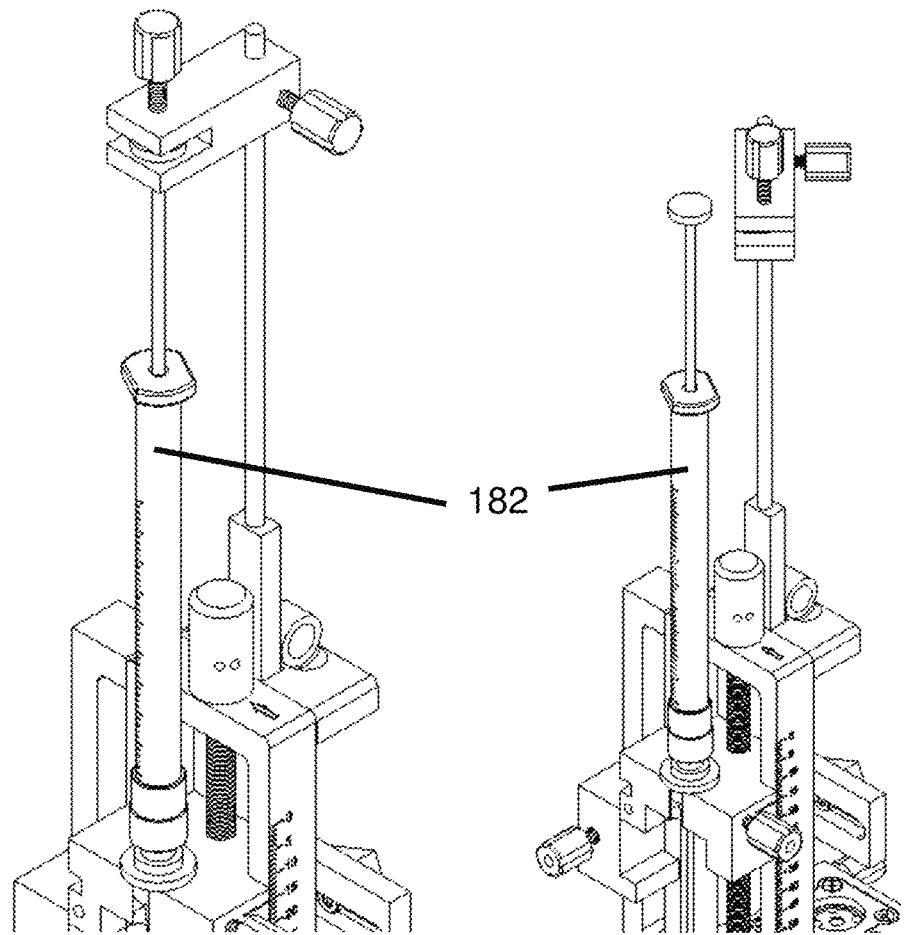

As shown in FIG. 8H, when cannula (192) has reached the target site, drive/motor stops advancement, and carriage connector (160) can be secured to the frame (120), in some aspects the side portion/u-slot (130), for example through fastener (158). When carriage connector (160), and consequently drive plate (154) have been secured in place, as shown in FIGS. 8I-8J, withdrawal of the cannula (192) and delivery of the therapeutic substance through syringe (182) can be initiated. Controlled the speed of drive/motor and positioning of the lever plate (166) can provide a precisely controlled rate of injection of the therapeutic substance along a defined path, providing a desired therapeutic distribution of the substance. As shown in FIGS. 8K-8L, once delivery of the therapeutic substance has been completed, the syringe (182) and/or cannula (192) can be removed from the device (100), for example by loosening clamps (188 and/or 190).

With reference to FIGS. 10-13, shown is another non-limiting aspect of a device (1000) as described herein. In the illustrated, non-limiting aspect, hydraulic probe drives, for example those available commercially from FHC, Inc. (Bowdoin, ME), rather than mechanical, screw-based drives, are utilized. However, it will be appreciated that the arrangement shown in FIGS. 10-13 will be suitable for mechanical as well as hydraulic drives. Further, it will be appreciated that multiple drives can be utilized to allow multiple injections at the same rate and in some non-limiting aspects simultaneously.

With reference to FIGS. 10-13, device (1000) includes frame (1020), hydraulic probe drives including pistons (1110, 1120) and cylinder barrels (1130, 1140), carriage plate (1052), drive plate (1054), lever plate (1066) connected thereto at pivot points (1070), and a fastener (1062) to allow for relative motion of the pistons and controlled drug delivery, or substance withdrawal, as described previously. Also included is a mechanical motor (not pictured) that can be attached to drive 1 (1110, 1130) or drive 2 (1120, 1140). Any drive not connected to a motor may freely move within the vertical tracks within the frame (1020). In the illustrated aspect, the motor (not shown) is attached to drive 1 (1110, 1130), which controls the motion of the base of a syringe (not shown) on a stereotactic frame (not shown). Drive 2 can be mounted above drive 1 (as shown schematically in FIG. 11), from which position it can control motion of the plunger (not shown) of the syringe (not shown).

In the aspect illustrated in FIGS. 10-13, a drive mode (FIGS. 10 and 12) is enabled in which the lever plate (1066) is locked to remain horizontal, and all linkage points (1070, 1070, 1062) are free to move vertically. In this way, the pistons (1110, 1120) move together as the motor (not shown) controls drive 1 to advance/retract the pistons (1110, 1120). This allows a user to adjust a starting point for an injection. Once the syringe needle is at the appropriate target, the drive plate (1054) is locked into place in a similar manner previously described herein, for example through a fastener utilizing a compression fit, friction fit, or other type of reversible or irreversible fastening. A lock on the lever plate (1066) may then be removed to allow rotation of the lever plate (1066) about the fastener (1062).

Figure 13:
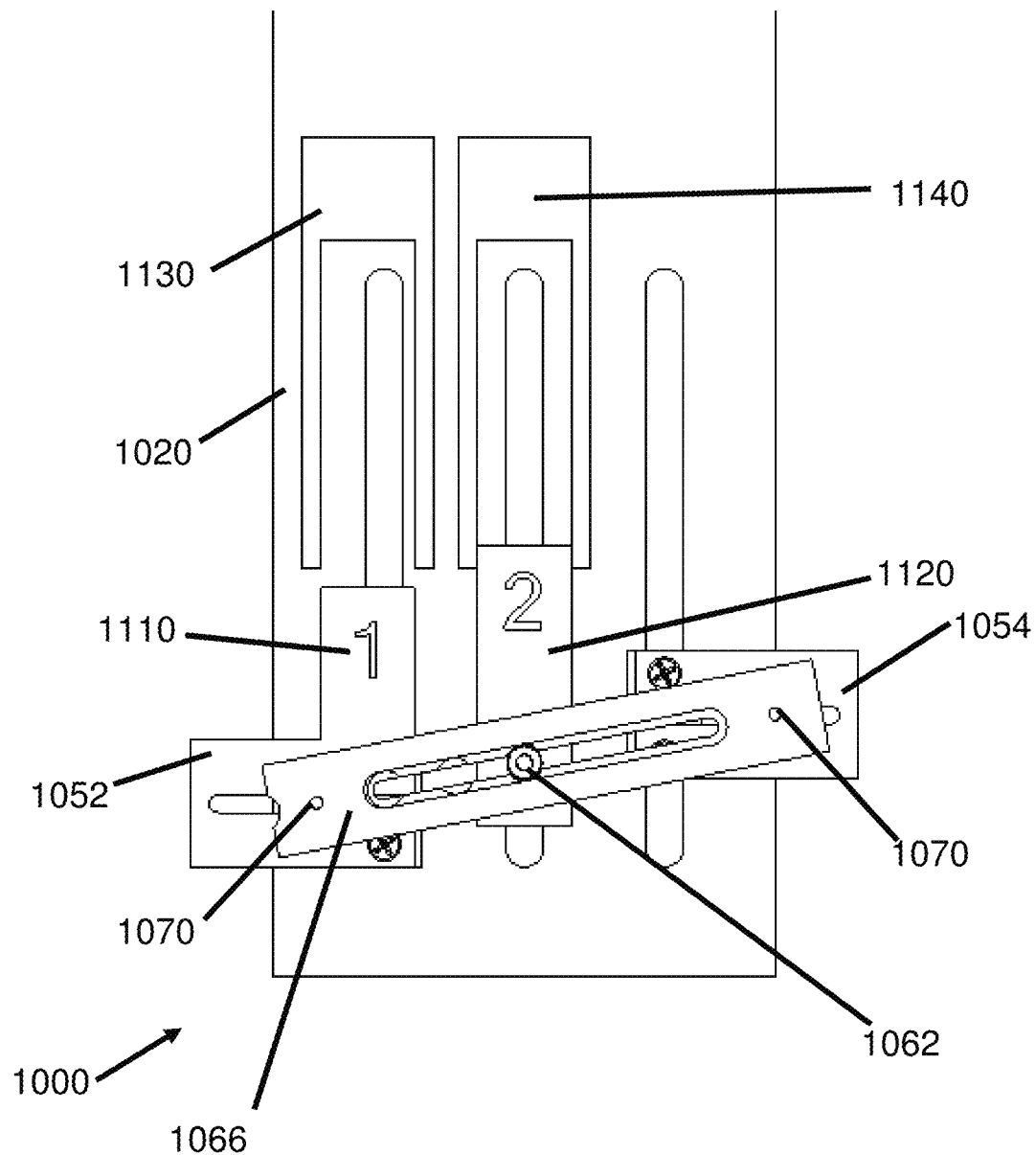
FIG. 13 shows a back view of a device according to one non-limiting aspect of the invention described herein.

With reference to FIG. 13, as the motor moves the piston of drive 1 (1110), the piston of drive 2 (1120) moves at a different rate because of the arrangement of the lever plate (1066) and fastener (1062), as previously described. This results in the syringe (not shown) being withdrawn while the plunger (not shown) injects desired medicament at the desired injection rate, as described previously. The injection rate can be adjusted by adjusting the location of the fastener (1062).

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for controlling relative delivery of a therapeutic during a surgical intervention, comprising:
    a base;
    a frame having a proximal end and a distal end attached to the base;
    a first subassembly comprising:
        a syringe carriage configured to interface with the frame and be moveable relative thereto and to hold a syringe for delivery of the therapeutic;
        a plunger shaft having a proximal end and a distal end, the plunger shaft directly connected at its distal end to the frame; and
        an instrument clamp adjustably connected to the plunger shaft by a friction fit; and
    a syringe comprising a delivery cannula attached to a syringe body and a syringe plunger received within the syringe body, the syringe at least partially held by the syringe carriage,
    wherein the system is configured such that, when the syringe plunger is secured to the instrument clamp, as the delivery cannula is withdrawn from a target, the syringe plunger is held in place by the instrument clamp such that the syringe plunger moves relative to the syringe body to cause delivery of the therapeutic as the syringe carriage moves and the delivery cannula is withdrawn.

2. The system of claim 1, further comprising:
    a second subassembly comprising:
        a carriage plate;
        a drive plate;
        a lever plate comprising one or more openings and connected to the carriage plate and the drive plate; and a fastener connecting the lever plate to the plunger shaft through one of the one or more openings of the lever plate, wherein interaction of the fastener, the one or more openings of the lever plate, and the plunger shaft controls a rate of delivery of the therapeutic during withdrawal of the delivery cannula.

3. The system according to claim 2, wherein the one or more openings in the lever plate correspond to one or more injection rates.

4. The system according to claim 2, wherein the one or more openings in the lever plate comprise an elongated opening with one or more seats for the fastener.

5. The system according to claim 4, wherein the one or more seats correspond to one or more injection rates.

6. The system according to claim 2, wherein the first subassembly further comprises a carriage connector comprising a fastener configured to releasably connect the carriage connector to the frame.

7. The system according to claim 6, wherein, when the carriage connector is connected to the frame, the drive plate is configured to be held in place during withdrawal of the delivery cannula.

8. The system according to claim 6, further comprising one or more resiliently-biased members configured to resiliently bias the carriage connector against the syringe carriage while the carriage connector is not connected to the frame.

9. The system according to claim 1, further comprising a fastener configured to releasably connect the syringe to the syringe carriage.

10. The system according to claim 1, further comprising one or more fasteners configured to releasably connect the syringe plunger to the instrument clamp.

11. The system according to claim 1, further comprising one or more fasteners configured to hold the instrument clamp at a relative location along the plunger shaft.

12. The system according to claim 1, further comprising a motor or a drive for advancing and withdrawing the syringe carriage along a longitudinal axis of the system.

13. The system according to claim 1, further comprising a frame adapter, connected to the base of the system and configured to connect the system to a stereotactic frame.

14. The system of claim 1, further comprising one or more computing devices.

15. The system of claim 14, wherein the one or more computing devices are configured to control, through one or more motors or drives, one or more of:
   a rate of advancement of the delivery cannula to the target within a patient; and
   a rate of withdrawal of the delivery cannula from a target within a patient.

16. The system of claim 1, wherein the system is configured such that a ratio of movement of the syringe plunger relative to the syringe body:the delivery cannula withdrawal is 1:1.

\* \* \* \* \*

UNITED STATES PATENT AND TRADEMARK OFFICE
CERTIFICATE OF CORRECTION

PATENT NO. : 12,311,150 B2
APPLICATION NO. : 17/356948
DATED : May 27, 2025
INVENTOR(S) : Frederick A. Haer et al.

Page 1 of 1

It is certified that error appears in the above-identified patent and that said Letters Patent is hereby corrected as shown below:

In the Claims

Column 16, Line 22, Claim 15, delete "a target" and insert -- the target --

Signed and Sealed this
Second Day of September, 2025

Coke Morgan Stewart
*Acting Director of the United States Patent and Trademark Office*